(12) United States Patent
Van Immerseel et al.

(10) Patent No.: US 10,576,052 B2
(45) Date of Patent: *Mar. 3, 2020

(54) COMPOSITION PREVENTING BACTERIAL INFLAMMATION IN MONOGASTRIC ANIMALS

(71) Applicant: PERSTORP AB, Perstorp (SE)

(72) Inventors: Filip Van Immerseel, Eke (BE); Karolien Van Driessche, Zele (BE); Richard Ducatelle, Wortegem-Petegem (BE); Conrad Gerard Schwarzer, Beringen (BE)

(73) Assignee: PERSTORP AB, Perstorp (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/775,705

(22) PCT Filed: Nov. 10, 2016

(86) PCT No.: PCT/SE2016/000066
§ 371 (c)(1),
(2) Date: May 11, 2018

(87) PCT Pub. No.: WO2017/082791
PCT Pub. Date: May 18, 2017

(65) Prior Publication Data
US 2018/0353456 A1   Dec. 13, 2018

(30) Foreign Application Priority Data

Nov. 13, 2015   (SE) ..................................... 1500460

(51) Int. Cl.
*A61K 31/22*   (2006.01)
*A23K 20/158*   (2016.01)
(Continued)

(52) U.S. Cl.
CPC ............ *A61K 31/22* (2013.01); *A23K 20/158* (2016.05); *A23K 50/70* (2016.05); *A23L 33/12* (2016.08); *A61K 31/215* (2013.01)

(58) Field of Classification Search
None
See application file for complete search history.

(56) References Cited

U.S. PATENT DOCUMENTS

2018/0141820 A1*   5/2018   Zhang .................. C01B 33/128

FOREIGN PATENT DOCUMENTS

EP           2215913 A1    8/2010
WO       2006085346    *   8/2006
(Continued)

OTHER PUBLICATIONS

SE 1500157, downloaded from https://patents.google.com/patent/SE1500157A1/en?oq=se+1500157 (Year: 2016).*
(Continued)

*Primary Examiner* — Karl J Puttlitz
(74) *Attorney, Agent, or Firm* — Polsinelli PC

(57) ABSTRACT

The present invention refers to a glycerol ester composition comprising glyceryl monovalerate, for use in preventing and/or alleviating bacterial inflammation in a monogastric animal (including human) by inhibiting the adhesion of pathogenic bacteria to the intestinal lumen of said animal. The present invention also refers to a therapeutic method for promoting the renewal and growth of epithelial cells in the small intestine of a monogastric animal (including human), the method comprising the step of distributing a glycerol ester composition comprising glyceryl monovalerate to said animal.

18 Claims, 1 Drawing Sheet

(51) Int. Cl.
*A23K 50/70* (2016.01)
*A23L 33/12* (2016.01)
*A61K 31/215* (2006.01)

(56) References Cited

FOREIGN PATENT DOCUMENTS

| WO | 2006085346 | A1 |   | 8/2006 |
|---|---|---|---|---|
| WO | 2010106488 | A2 |   | 9/2010 |
| WO | 20101064881 |   | * | 9/2010 |
| WO | 2011002298 |   | * | 1/2011 |
| WO | 2011002298 | A2 |   | 1/2011 |
| WO | 2015057122 | A1 |   | 4/2015 |
| WO | 2016093757 | A1 |   | 6/2016 |
| WO | 2016159853 |   | * | 10/2016 |
| WO | 2016159853 | A1 |   | 10/2016 |

OTHER PUBLICATIONS

International Search Report and Written Opinion dated Feb. 2, 2017 in the PCT Application No. PCT/SE2016/000066.

Manuela Parini, Challenges and New Tendencies in Use of Lipids for Animal Nutrition, Cost, European Cooperation in Science and Technology, Milano, 2009, pp. 1-32.

Mauro Antongiovanni et al., "Butyric acid glycerides in the diet of broiler chickens: effects on the gut histology and carcass composition," Italian Journal of Animal Science, 2007, vol. 6, pp. 19-25.

Marc Sutter et al., "1-O-Alkyl (di)glycerol ethers synthesis from methyl esters and triglycerides by two pathways: catalytic reductive alkylation and transesterification/reduction," Green Chemistry, 2013, vol. 15, pp. 786-797.

Matthias Berger et al., "Enzymatic Esterification of Glycerol II. Lipase-Catalyzed Synthesis of Regioisomerically Pure 1(3)-rac-Monoacylglycerols," Journal of American Oil Chemists' Society, 1992, vol. 69, No. 10, pp. 961-965.

* cited by examiner

COMPOSITION PREVENTING BACTERIAL INFLAMMATION IN MONOGASTRIC ANIMALS

CROSS-REFERENCE TO RELATED APPLICATIONS

This application is a national stage application (under 35 U.S.C. § 371) of PCT/SE2016/000066, filed Nov. 10, 2016, which claims benefit of European Application No. 1500460.9, filed Nov. 13, 2015, which are incorporated herein by reference in their entireties.

FIELD OF THE INVENTION

The present invention refers to a glycerol ester composition comprising glyceryl monovalerate, for-use in preventing and/or alleviating bacterial inflammation in a monogastric animal (including human) by inhibiting the adhesion of pathogenic bacteria to the intestinal lumen of said animal.

The present invention also refers to a therapeutic method for promoting the renewal and growth of epithelial cells in the small intestine of a monogastric animal (including human), the method comprising the step of distributing a glycerol ester composition comprising glyceryl monovalerate to said animal.

BACKGROUND OF THE INVENTION

The immune system of a monogastric animal is to a large extent located in the gut region. The immune system on the gut level is influenced in different ways by the feed that is ingested by the animal. Naturally, a good uptake of nutrients by the animal results in a better general health, a better growth and a better resistance against diseases for the animal. However, more and more evidence has become available on the fact that specific components in the animal's diet can have a more direct impact on the immune system at the gut level.

In monogastric animals, like pigs and chicken, the digestive system is simpler compared with ruminants, like cows and goats. The small intestine is the part of the gastrointestinal tract between the stomach and the large intestine, and is where much of the digestion and absorption of food takes place. The small intestine has three distinct regions—the duodenum, jejunum, and ileum. The primary function of the small intestine is the absorption of nutrients and minerals from food, but it is also an important part of the immune system on the gut level. The small intestine is covered by a mucosal tissue where a continuously regenerating mucus layer serves as protection against harmful microorganisms and toxins.

Intestinal villi are small, finger-like projections that protrude from the epithelial lining of the intestinal wall. They are covered predominantly with mature, absorptive enterocytes, along with occasional mucus-secreting goblet cells. Villi increase the internal surface area of the intestinal walls making available a greater surface area for absorption. An increased absorptive area is useful because digested nutrients (including monosaccharide and amino acids) pass into the semipermeable villi through diffusion, which is effective only at short distances. In other words, increased surface area (in contact with the fluid in the lumen) decreases the average distance travelled by nutrient molecules, so effectiveness of diffusion increases. The villi are connected to the blood vessels so the circulating blood then carries these nutrients away. Crypts are moat-like invaginations of the epithelium around the villi, and are lined largely with younger epithelial cells which are involved primarily in secretion. Toward the base of the crypts are stem cells, which continually divide and provide the source of all the epithelial, cells in the crypts and on the villi.

It is commonly known in the art that various short chain fatty acids as well as their respective glycerol monoesters seem to have different positive effects on animal health. For example, butyric acid helps to maintain and restore the integrity of the gut by stimulating cell proliferation and growth of the intestinal villi.

There are several benefits associated with distributing short chain fatty acids as glycerol esters. Glycerol esters are less corrosive than the corresponding free acids, facilitating handling and transportation of the products. Some of the short chain fatty acids, like for example butyric acid and valeric acid, have a very unpleasant smell. The corresponding glycerol esters of these acids are more or less odorless. Additionally, glycerol esters bind the short chain fatty acids, enabling them to reach further down in the gastrointestinal tract of a human or an animal before being adsorbed to the bloodstream.

It is known from SE1500157-1 that glycerol ester compositions comprising a high amount of glyceryl monovalerate inhibits the growth of gram positive bacteria, like for example *Clostridium perfringens*, and that such compositions prevent the prevalence of the disease necrotic enteritis in galloanserae.

It has now further been found that the renewal and growth of epithelial cells in the small intestine of a monogastric animal is significantly improved when the animal is fed a glycerol ester composition comprising glyceryl monovalerate. This in turn helps to maintain the lumen in a healthy, intact state, preventing pathogenic bacteria from adhering to the intestinal lumen and causing a bacterial inflammation. Glyceryl monovalerate has also been found to inhibit the growth of pathogenic bacteria as well as to reduce the invasiveness of these bacteria. This means that glyceryl monovalerate can be used in a multifunctional way to inhibit the adhesion of pathogenic bacteria to the intestinal lumen of monogastric animals, and thereby prevent bacterial inflammation in these animals.

DETAILED DESCRIPTION OF THE INVENTION

Figure 1:
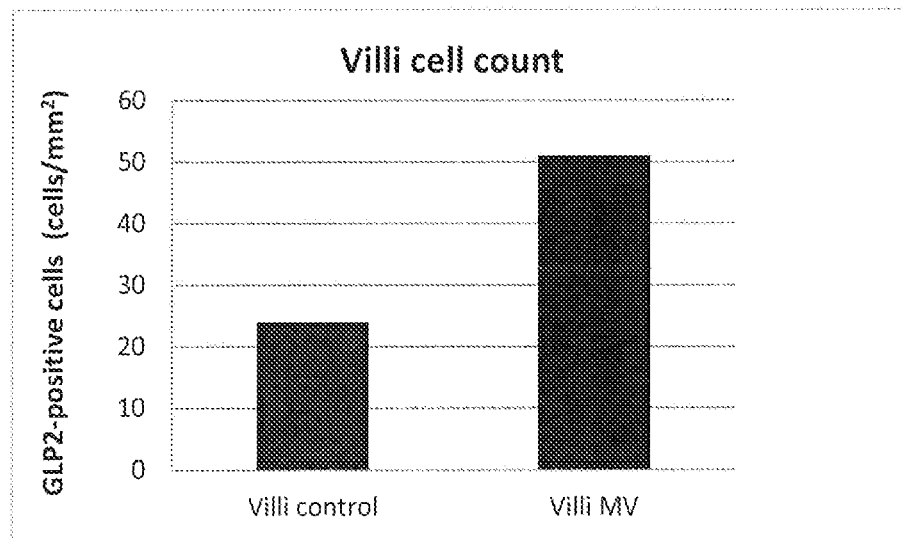
FIG. 1 is a graph showing the average numbers of GLP2-positive cells detetced in the villi of jejunum and ileum of birds in a control group and birds ain an an experimental group.

The present invention refers to a glycerol ester composition comprising glyceryl monovalerate, for use in preventing and/or alleviating bacterial inflammation in a monogastric animal (including human) by inhibiting the adhesion of pathogenic bacteria to the intestinal lumen of said animal. Monogastric animals include for example humans, pets, pigs, horses, poultry and aquatic species. These species have a digestive system that is considerably simpler compared with ruminants, like cows and goats Glyceryl monovalerate can be used in several different ways to prevent pathogenic bacteria from adhering to the intestinal lumen of a monogastric animal.

According to one embodiment of the present invention the adhesion of pathogenic bacteria to the intestinal lumen is inhibited by promoting the renewal and growth of epithelial cells in the small intestine of the monogastric animal. A luminal structure with well-defined and well-developed villi and crypts will keep the intestinal surface intact and, hence, more resistant to adhesion of pathogenic bacteria. A healthy luminal structure will also result in an improved nutrient uptake, which will contribute to strengthening the animal's resistance against pathogens.

According to another embodiment of the present invention the adhesion of pathogenic bacteria to the intestinal lumen is inhibited by inhibiting the growth of said pathogenic bacteria. In vitro experiments have shown that glyceryl monovalerate is an effective inhibitor of for example *Salmonella* growth.

According to still another embodiment of the present invention the adhesion of pathogenic bacteria to the intestinal lumen is inhibited by reducing the invasiveness of said pathogenic bacteria. It has been seen in experiments that invasive gene expression (HilA expression) in *Salmonella* is down-regulated by glyceryl monovalerate.

According to one embodiment of the present invention, the pathogenic bacteria belong to the family Enterobacteriaccae such as to the genera *Escherichia coli* and/or *Salmonella*.

*Escherichia coli* strains can cause gastroenteric diseases, such as diarrhea and hemorrhagic colitis in many monogastric animals and even mortality in young pigs.

*Salmonella* disturbs the immune system in poultry and pigs, making them more vulnerable for diseases. Humans that eat infected eggs or meat develop symptoms like diarrhea, fever and vomiting and can get dangerously dehydrated.

According to a preferred embodiment of the present invention, the monogastric animal belongs to the clade galloanserae. Galloanserae include both galliformes, like for example chicken, and anseriformes, like for example turkey. The worldwide consumption of meat from these animals has increased heavily and will, most likely, continue to increase. Consequently, the economic impact of this industry is also increasing and it is of great importance to improve and maintain a healthy status of the digestive system of these animals.

Most of the nutrient uptake of a monogastric animal occurs in the small intestine, through the intestinal structures called villi and crypts. Villi are small, finger-like projections that protrude from the epithelial lining of the intestinal wall. They are covered predominantly with mature, absorptive enterocytes, along with occasional mucus-secreting goblet cells. Villi increase the internal surface area of the intestinal walls making available a greater surface area for absorption. The villi are connected to the blood vessels so the circulating blood then carries these nutrients away. Crypts are moat-like invaginations of the epithelium around the villi, and are lined largely with younger epithelial cells which are involved primarily in secretion. Toward the base of the crypts are stem cells, which continually divide and provide the source of all the epithelial cells in the crypts and on the villi.

The surface area of the villi and the crypts in the small intestine is directly linked to the nutrient utilization of the feed: a greater surface area of these structures results, in a more efficient uptake of nutrients from the feed. This will improve the general health of the animal and make it more resistant to pathogens. Glyceryl monovalerate has now also been found to act specifically in at least three different ways to prevent and/or alleviate bacterial inflammation in monogastric animals by inhibiting the adhesion of pathogenic bacteria to the intestinal lumen: it promotes the renewal and growth of epithelial cells in the intestinal lumen, it inhibits the growth of pathogenic bacteria and it also reduces the invasiveness of pathogenic bacteria.

In the context of the present invention, glyceryl monovalerate is understood to be the reaction product obtained from reacting valeric acid and glycerol at about equimolar ratio or a molar ratio of between 1:0.8 and 1:1.2. If glycerol and fatty acid are allowed to react through direct esterification, an equilibrium will form between fatty acid, glycerol, monoglyceride, diglyceride and triglyceride. The main reaction is fatty acid and glycerol reacting to form monoglycerides and water, but secondary reaction (monoglyceride and fatty acid reacting to diglyceride and water) and tertiary reaction (diglyceride and fatty acid reacting to triglyceride and water) cannot be avoided as it happens simultaneously. Factors like the availability of water and temperature will influence the equilibrium and internal hydrolyzation as well as re-esterification will most probably occur to some extent. Consequently, it is not trivial to define exactly how the distribution of mono-, di- and tri-ester will be in the product.

According to one embodiment of the present invention, the glycerol ester composition comprises at least 30% by weight of glyceryl monovalerate, below 20% by weight of glyceryl divalerate and below 5% by weight of glyceryl trivalerate.

According to a preferred embodiment of the present invention, the glycerol ester composition comprises at least 40% by weight of glyceryl monovalerate, below 15% by weight of glyceryl divalerate and below 2% by weight of glyceryl trivalerate.

Free valeric acid has an unpleasant smell, which causes handling problems. These problems can be avoided by distributing the valeric acid in the form of glycerol esters. According to one embodiment of the present invention, the amount of free valeric acid in the glycerol ester composition is below 0.5% by weight, preferably below 0.1% by weight. Keeping down the amount of free valeric acid also ensures that the pH in the glycerol ester composition is kept at a level where hydrolyzation of the glycerol ester into glycerol and free acid is suppressed; so that the product is kept stable.

The glycerol ester composition comprising glyceryl monovalerate is fed to the monogastric animal in an amount between 0.01 and 1.0%, preferably between 0.05 and 0.7%, by weight of the animal's daily feed ration.

The renewal and growth of epithelial cells in the small intestine can be quantified by measuring the average number of so called "GLP-2 positive, cells" in villi and crypts of the small intestine, using computerized methods for cell counting known in the art. In the context of the present invention, "average cell count" is understood to be the same, as "average number of GLP-2 positive cells".

According to one embodiment of the present invention, the average cell count in the small intestine is increased by at least 20%, preferably at least 40%, after said glycerol ester composition is fed to said animal, as calculated on a time period of 10 days of treatment.

According to another embodiment of the present invention, the average cell count in the villi in the small intestine is increased by at least 80% after said glycerol ester composition is fed to said animal, as calculated on a time period of 10 days of treatment.

According to one embodiment of the present invention the glycerol ester composition is adsorbed on an inert carrier, such as a silica carrier. This allows the composition to be distributed as a dry product. Distributing the glycerol ester composition adsorbed on a silica carrier contributes to keeping down the amount of free water in the composition and thereby inhibiting the hydrolyzation of glycerol ester into glycerol and free acid. The product is kept more stable and the odor problems associated with free valeric acid are minimized. From for instance CA1168078, glycerol is well-known as a water-binder in animal food. Additional glycerol may be added to the glycerol ester composition according to the invention in order to minimize the content of reactable water. At the same time, the energy content of the composition is raised, since glycerol has about the same amount of nutritional energy as glucose.

The glycerol ester composition for use according to the present invention can be added to any commercially available feedstuffs for monogastric animals. The glycerol ester composition may be incorporated directly into commercially available feeds or fed supplementary to commercially available feeds. The glycerol ester composition for use according to the present invention can also be added to the drinking water.

The present invention further refers to a therapeutic method for promoting the renewal and growth of epithelial cells in the small intestine of a monogastric animal (including human), the method comprising the step of distributing a glycerol ester composition comprising glyceryl monovalerate to said animal.

According to one embodiment of the present invention, the adhesion of pathogenic bacteria to the intestinal lumen of said animal in inhibited.

According to another embodiment of the present invention, the growth of said pathogenic bacteria is inhibited.

According to still another embodiment of the present invention, the invasiveness of said pathogenic bacteria is reduced.

According to a preferred embodiment of the present invention, the pathogenic bacteria are Enterobacteriaceae such as *Escherichia coli* and/or *Salmonella*.

The present invention is further explained with reference to the enclosed Embodiment Example, which is to be construed as illustrative and not limiting in any way.

EMBODIMENT EXAMPLE

Animals and Housing.

27 one-day-old Ross broiler chickens were obtained from a local hatchery. The animals were divided at random in two equal groups: one experimental groups, and one control group. The groups were housed on wood shavings in separate containers of 0.96 m$^2$. Commercial feed and drinking water was provided ad libitum, From the day of hatch, the experimental group received feed supplemented with glyceryl monovalerate (MV; Perstorp, 5.6 g/kg feed), according to the suppliers recommendations (in-feed supplementation). The control group, received unsupplemented feed. At the age of ten days, the animals were killed by injecting an intravenous overdose of pentobarbital and sampling was performed.

Sampling.

Samples (1 cm in length) of jejunum and ileumn were submerged in 4% phosphate buffered (wt/vol) formaldehyde within 15 minutes after euthanasia. After fixation for 24 h the samples were processed routinely, embedded in paraffin wax and sections with 5 μm thickness were made.

Immunohistochemistry.

The slides were deparaffinised and rehydrated. Heat-induced antigen retrieval was performed in citrate buffer (pH=6.0). The slides were incubated with 3% $H_2O_2$ in methanol for 5 minutes in order to block endogenous peroxidase activity. In order to prevent non-specific reactions, the slides were incubated in 30% goat serum for 30 minutes. Rabbit anti-human GLP-2 (diluted 1:1000; Phoenix Pharmaceuticals Inc., Burlingame, USA) was used as primary antibody to stain GLP-2 antigen. The sections were further performed with Envision+System-HPR (DAB) (DakoCytomation, Glostrup, Denmark) for visualization. Counterstaining of the nuclei was done with haematoxylin. Finally, slides were dehydrated and mounted.

Quantification of GLP-2 Positive Cells.

For each animal, the area of 10 randomly chosen villi and 30 randomly chosen crypts was measured for jejunum and ileum using LAS V3.8 software (Leica Microsystems GmbH, Wetzlar, Germany). In total 80 areas per bird were analysed. For every defined area, the number of cells was counted at magnification ×400. Only cells with a detectable nucleus were counted. The average number of cells per area villus or crypt (cells/mm$^2$) was calculated for each bird.

Statistical Analysis.

A Kruskal-Wallis with Dunn's test (posthoc-test) was used to determine statistical differences on the number of cells/mm$^2$ between the different groups for the villi and crypts respectively. Differences with P-values lower than 0.05 were considered to be significant.

RESULTS

The average numbers of GLP2-positive cells detected in the villi of jejunum and ileum of birds in the control group and birds in the experimental group respectively are shown in FIG. 1. The average number of GLP-2 positive cells was statistically higher in the experimental group than in the control group (P≤0.001).

Figure 2:
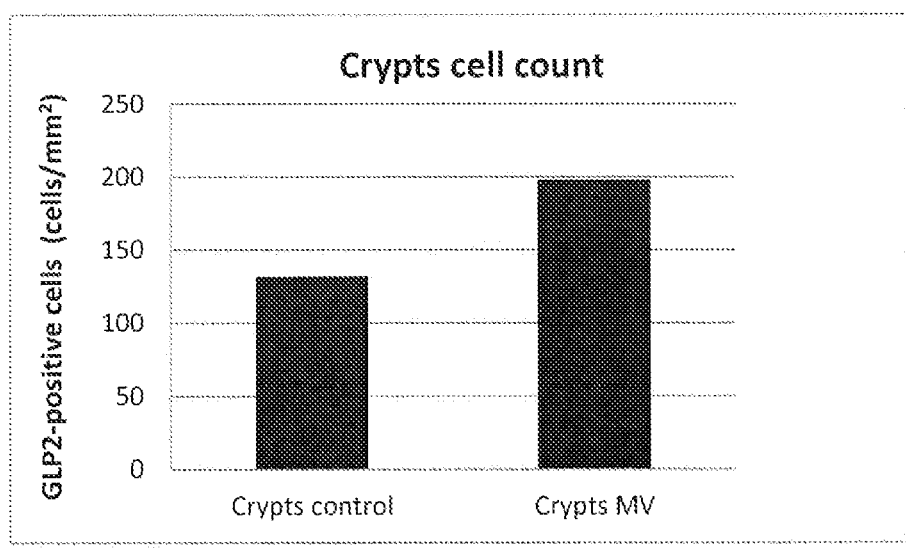
FIG. 2 is a graph showing the average numbers of GLP2-positive cells detected in the crypts of jejunum and ileum of birds in a control group and birds in an expeimental groups.

Also for the crypts, the average numbers of GLP2-positive cells in jejunum and ileum was statistically higher in the experimental group compared to the control group (P≤0.05). Results are shown in FIG. 2.

These results clearly show that glyceryl monovalerate stimulates the renewal and growth of epithelial cells in the small intestine. The improved luminal structure of the small intestine will inhibit the adhesion of pathogenic bacteria to the intestinal lumen and prevent and/or alleviate bacterial inflammation in the animal.

The invention claimed is:

1. A therapeutic method for inhibiting the growth of pathogenic bacteria in the small intestine of a monogastric animal in need thereof, the method comprising administering a glycerol ester composition comprising at least 40% by weight of glyceryl monovalerate to said animal.

2. A method according to claim 1, wherein the adhesion of pathogenic bacteria to the intestinal lumen of said animal in inhibited.

3. A method according to claim 2, wherein the invasiveness of said pathogenic bacteria is reduced.

4. A method according to claim 2, wherein said pathogenic bacteria are Enterobacteriaceae.

5. A method according to claim 4, wherein the Enterobacteriaceae are *Escherichia coli*.

6. A method according to claim 4, wherein the Enterobacteriaceae are *Salmonella*.

7. A method according to claim 1, wherein said monogastric animal is a galloanserae.

8. A method according to claim 1, wherein said monogastric animal is a galliform.

9. A method according to claim 1, wherein said monogastric animal is an anseriform.

10. A method according to claim 1, wherein said glycerol ester composition is fed to said animal in an amount between 0.01 to 1.0% by weight of the animal's daily feed ration.

11. A method according to claim 1, wherein said glycerol ester composition is fed to said animal in an amount between 0.05 to 0.7% by weight of the animal's daily feed ration.

12. A method according to claim 10, wherein the average cell count in the small intestine is increased by at least 20% after said glycerol ester composition is fed to said animal for 10 days.

13. A method according to claim 10, wherein the average cell count in the small intestine is increased by at least 40% after said glycerol ester composition is fed to said animal for 10 days.

14. A method according to claim 10, wherein the average cell count in the villi in the small intestine is increased by at least 80% after said glycerol ester composition is fed to said animal for 10 days.

15. A method according to claim 1, wherein said glycerol ester composition is adsorbed on a carrier thereby allowing said glycerol ester composition to be distributed as a dry product.

16. A method according to claim 15, wherein the carrier is silica.

17. The method of claim 1, wherein the composition includes at least 1.5 fold more glyceryl monovalerate than glyceryl divalerate and at least 8 fold more glyceryl monovalerate than glyceryl trivalerate.

18. The method of claim 1, wherein the glyceryl ester composition is added to drinking water for administration to said animal.

* * * * *